(12) United States Patent
Van Deusen et al.

(10) Patent No.: US 9,897,575 B2
(45) Date of Patent: Feb. 20, 2018

(54) DIAGNOSTIC TESTING SENSORS FOR RESONANT DETECTORS

(71) Applicant: Qorvo US, Inc., Greensboro, NC (US)

(72) Inventors: Richard A. Van Deusen, St. Paul, MN (US); Ian R. Harmon, Minneapolis, MN (US)

(73) Assignee: QORVO US, INC., Greensboro, NC (US)

( * ) Notice: Subject to any disclaimer, the term of this patent is extended or adjusted under 35 U.S.C. 154(b) by 178 days.

(21) Appl. No.: 14/714,710

(22) Filed: May 18, 2015

(65) Prior Publication Data

US 2015/0268197 A1 Sep. 24, 2015

Related U.S. Application Data

(63) Continuation of application No. 13/162,353, filed on Jun. 16, 2011, now Pat. No. 9,032,782.

(60) Provisional application No. 61/355,409, filed on Jun. 16, 2010.

(51) Int. Cl.
*G01N 29/036* (2006.01)
*G01N 33/50* (2006.01)
*G01N 29/02* (2006.01)
*G01N 29/30* (2006.01)

(52) U.S. Cl.
CPC ......... *G01N 29/036* (2013.01); *G01N 29/022* (2013.01); *G01N 29/30* (2013.01); *G01N 33/50* (2013.01); *G01N 2291/0255* (2013.01); *G01N 2291/0256* (2013.01); *G01N 2291/0427* (2013.01)

(58) Field of Classification Search
CPC .... G01N 29/036; G01N 29/30; G01N 29/022; G01N 33/50; G01N 2291/0255; G01N 2291/0256
USPC ........... 73/61.41, 61.43, 61.45, 61.49, 61.79, 73/64.53; 204/403.1, 403.2, 403.03, 204/403.04, 403.02; 205/770, 792; 600/583
See application file for complete search history.

(56) References Cited

U.S. PATENT DOCUMENTS

| 5,231,327 | A | * | 7/1993 | Ketcham | ................ | H03H 9/568 |
| | | | | | | 310/320 |
| 5,932,953 | A | | 8/1999 | Drees et al. | | |
| 6,054,277 | A | | 4/2000 | Furcht et al. | | |
| 6,303,288 | B1 | | 10/2001 | Furcht et al. | | |

(Continued)

*Primary Examiner* — Laura Martin
*Assistant Examiner* — Rose M Miller
(74) *Attorney, Agent, or Firm* — Mueting, Raasch & Gebhardt, P.A.

(57) ABSTRACT

Biosensor apparatus and associated method for detecting a target material using a vibrating resonator having a surface that operably interacts with the target material. A detector is in electrical communication with a sensor, the sensor comprising a first paddle assembly connected to a second paddle assembly, the first paddle assembly having at least one microbalance sensing resonator proximate a proximal end and at least one sensing electrical contact proximate a distal end in electrical communication with the sensing resonator. The at least one sensing resonator has a target coating for operably interacting with the target material, and the second paddle assembly has a microbalance reference resonator proximate the proximal end and at least one reference electrical contact proximate the distal end in electrical communication with the reference resonator.

7 Claims, 16 Drawing Sheets

(56) References Cited

U.S. PATENT DOCUMENTS

| | | | |
|---|---|---|---|
| 8,323,467 B2 * | 12/2012 | MacFie | G01N 27/3272 204/267 |
| 9,032,782 B1 | 5/2015 | Van Deusen et al. | |
| 2003/0103867 A1 | 6/2003 | Newman et al. | |
| 2005/0225214 A1 | 10/2005 | Kalinin et al. | |
| 2007/0247245 A1 | 10/2007 | Hagelin | |
| 2008/0039339 A1 * | 2/2008 | Hassibi | C12Q 1/6818 506/9 |
| 2008/0160635 A1 | 7/2008 | Castro et al. | |
| 2009/0243747 A1 * | 10/2009 | Gaidarzhy | H03H 9/02409 333/17.1 |
| 2010/0095774 A1 * | 4/2010 | Sone | G01N 29/022 73/580 |

* cited by examiner

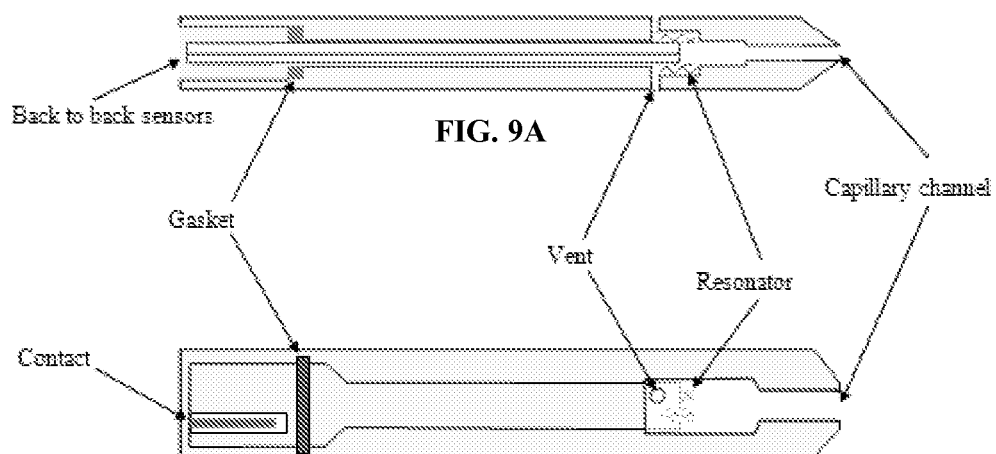
FIG. 9A
FIG. 9B
FIG. 10A
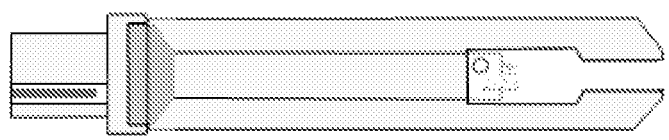
FIG. 10B

DIAGNOSTIC TESTING SENSORS FOR RESONANT DETECTORS

PRIOR APPLICATION

This application is a continuation application of U.S. application Ser. No. 13/162,353, filed Jun. 16, 2011, which claims priority to U.S. Provisional Application No. 61/355,409, filed Jun. 16, 2010, the contents of which are incorporated herein by reference thereto in their entirety.

FIELD OF THE INVENTION

The present invention relates to sensors, and more specifically to a sensor for diagnostic measuring or testing based on vibrating resonators that measure and compare a shift in resonance characteristics as it interacts with certain detected materials.

BACKGROUND OF THE INVENTION

There are a variety of sensors within the art for diagnostic testing of materials related to human health, veterinary medical, environmental, biohazard, bioterrorism, agricultural commodity and food safety. The means for diagnostic testing and analysis of chemical and/or biological materials at the point of need remains limited. Diagnostic testing traditionally requires long response times to obtain meaningful data, involves expensive remote or cumbersome laboratory equipment that costs thousands of dollars located in a centralized laboratory, requires large sample sizes, utilizes multiple reagents, demands highly trained users, may require numerous steps, and/or involves significant direct and indirect costs. For instance, in both the veterinary and human diagnostic markets, most tests require that a specimen be collected from the patient and sent to the laboratory, but the results are not available for several hours or days later. As a result, the patient may leave the caregiver's office without confirmation of the diagnosis and the opportunity to begin immediate treatment.

Other problems related to portable devices include diagnostic results that are limited in sensitivity and reproducibility compared to in-laboratory testing. Fast response times are desirable and often critical to the identification of chemical and/or biological materials, such as in providing timely medical attention or in averting the spread or exposure of public health threats. Direct costs relate to the labor, procedures, and equipment required for each type of analysis. Indirect costs partially accrue from the delay time before actionable information can be obtained, e.g., in medical analyses or in the monitoring of chemical processes. Many experts believe that the simultaneous diagnosis and treatment enabled by an effective point of need diagnostic testing system would yield clinical, economic and social benefits. For instance, clinical benefits include faster turnaround of results, reduced time to treatment, reduced disease severity and improved mortality/morbidity. Economic benefits included reduced length of stay, improved utilization, more efficient care delivery and fewer admissions. Social benefits include improved access to healthcare/therapy, higher patient satisfaction and reduced absenteeism.

Various technologies have been utilized to develop sensors to detect and analyze chemical and/or biological materials, but fail to address issues related to traditional detection and analysis systems. For example, some detection systems determine the presence of substances based on electrochemical reactions. Such electrochemical sensors, however, usually have complex sensor arrangements that require substance-recognizing agents, are expensive, are often difficult to miniaturize due to low current densities resulting from smaller sensor structural shapes, and the rate and efficiency of the electrochemical sensor response time may be undesirable as they are controlled by the chemical reactions. Other detection systems are known from chemical laboratory practice, such as the various types of chromatography and spectral analysis. The laboratory systems, however, often do not meet the demands for ruggedness, stability, transportability, and low maintenance and energy consumption required for diagnostic testing outside the laboratory. Bench-top instruments are also often very expensive and require a centralized laboratory to which samples must be sent for testing.

Resonators based on piezoelectric properties of materials have also been used in detecting very small quantities of materials. Piezoelectric resonators used as sensors in such applications are sometimes called "micro-balances." A piezoelectric resonator is typically constructed as a thin planar layer of crystalline piezoelectric material sandwiched between two electrode layers. When used as a sensor, the resonator is exposed to the material being detected to allow the material to bind on a surface of the resonator.

A conventional way of detecting the amount of the material bound on the surface of a sensing resonator is to operate the resonator as an oscillator at its resonant frequency, as described, for instance, in U.S. Pat. No. 5,932,953 entitled "Method and System for Detecting Material Using Piezoelectric Resonators," which is incorporated by reference herein. As the material being detected binds on the resonator surface, the oscillation frequency of the resonator is reduced. The change in the oscillation frequency of the resonator, caused by the binding of the material on the resonator surface, is measured and used to calculate the amount of the material bound on the resonator or the rate at which the material accumulates on the resonator surface.

The sensitivity of a piezoelectric resonator as a material sensor is typically proportional to its resonance frequency. Thus, the sensitivities of material sensors based on the popular quartz crystal resonators are limited by their relatively low oscillating frequencies, which typically range from several MHz to about 100 MHz. The development of thin-film resonator (TFR) technology has produced sensors with significantly improved sensitivities. A thin-film resonator is formed by depositing a thin film of piezoelectric material, such as AlN or ZnO, on a substrate. Due to the small thickness of the piezoelectric layer in a thin-film resonator, which is on the order of several microns ($\mu$m), the resonant frequency of the thin-film resonator is on the order of 1 GHz or higher. The high resonant frequencies and the corresponding high sensitivities make thin-film resonators useful for material sensing applications.

A significant disadvantage of the conventional approach is the difficulty in separating the real intended material binding signal from spurious environmental effects. During material detection, a sensing resonator is often exposed to different environmental conditions that also tend to alter the resonance properties of the resonator. It is often difficult to isolate the resonance changes caused by the material detected from the resonance changes caused by various environmental conditions without incorporating large, expensive means for environmental isolation.

What is still needed is a simple sensor and resonance shift detection system that is portable for point of need diagnostic testing of chemical and/or biological materials, which not only is simple to use with little or no training, but provides rapid turn-around of reproducibly consistent results at acceptable sensitivity levels, capable of embodiments that can be scaled for manufacturing level utilization, low cost, and capable of transmitting results anywhere to caregivers and patient information systems.

BRIEF SUMMARY OF THE INVENTION

Embodiments of the present invention meet the need for a simple, effective, cost-efficient, reliable, repeatable, sensor for resonance shift detection of chemical and/or biological materials. These sample materials are generally in the form of a fluid including, for instance, liquids, gasses, granular suspensions, gels, and the like. Resonance shift detection, in various embodiments, can be based on phase shift or frequency shift. In some embodiments of the invention, the resonance shift detection system includes a portable handheld resonance-shift detector and a sensor connected by an interconnector, that can be used for point of need diagnostic testing in the field. In other embodiments of the invention, the resonance shift detection system includes a laboratory bench resonance shift detector and a sensor connected by an interconnector. In still other embodiments, the resonance shift detector and sensor are directly connected without an interconnector.

One aspect of the invention is directed to a sensor for a biosensor instrument comprising a first paddle assembly and a second paddle assembly. The first paddle assembly includes a first substrate having a proximal end, a distal end, a front surface and a back surface, a microbalance sensing resonator assembly attached to the front surface of the first substrate proximate the proximal end, and at least one sensing electrical contact proximate the distal end in electrical communication with the sensing resonator assembly. The second paddle assembly is connected to the first paddle assembly, and includes a second substrate having a proximal end, a distal end, a front surface and a back surface, a microbalance reference resonator assembly attached to the front surface of the second substrate proximate the proximal end, and at least one reference electrical contact proximate the distal end in electrical communication with the reference resonator assembly. The first and second paddle assemblies are connected such that the sensing and reference resonator assemblies are on a proximal end of the sensor. The sensing resonator assembly comprises at least one sensing resonator coated with a testing material that operably interacts with a target material, such as by binding with the target material.

According to another aspect, an apparatus for detecting a target material includes a sensor having a proximate end and a distal end, the sensor comprising a first paddle assembly connected to a second paddle assembly, the first paddle assembly having at least one sensing resonator proximate the proximal end and at least one sensing electrical contact proximate the distal end in electrical communication with the sensing resonator, the second paddle assembly having a reference resonator proximate the proximal end and at least one reference electrical contact proximate the distal end in electrical communication with the reference resonator, wherein the at least one sensing resonator has a target coating for operably interacting with the target material, such as by binding to the target material. The apparatus further includes a detector in electrical communication with the sensor.

A method of detecting a target material according to another aspect of the invention includes providing an apparatus for detecting the target material, the apparatus comprising a detector in electrical communication with a sensor, the sensor comprising a first paddle assembly connected to a second paddle assembly, the first paddle assembly having at least one sensing resonator proximate a proximal end and at least one sensing electrical contact proximate a distal end in electrical communication with the sensing resonator, the at least one sensing resonator having a target coating for operably interacting with the target material, and the second paddle assembly having a reference resonator proximate the proximal end and at least one reference electrical contact proximate the distal end in electrical communication with the reference resonator. The method further includes contacting the sensing resonator and the reference resonator with a test sample.

The above summary of the various representative embodiments of the present invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 9A is a side perspective schematic of a sensor assembly within a sensor housing assembly according to one embodiment of the present invention.

FIG. 9B is a top perspective schematic of the sensor assembly within the sensor housing assembly of FIG. 9A.

FIG. 10A is a side perspective schematic of a sensor assembly within a sensor housing assembly according to one embodiment of the present invention.

FIG. 10B is a top perspective schematic of the sensor assembly within the sensor housing assembly of FIG. 10A.

Figure 1A:
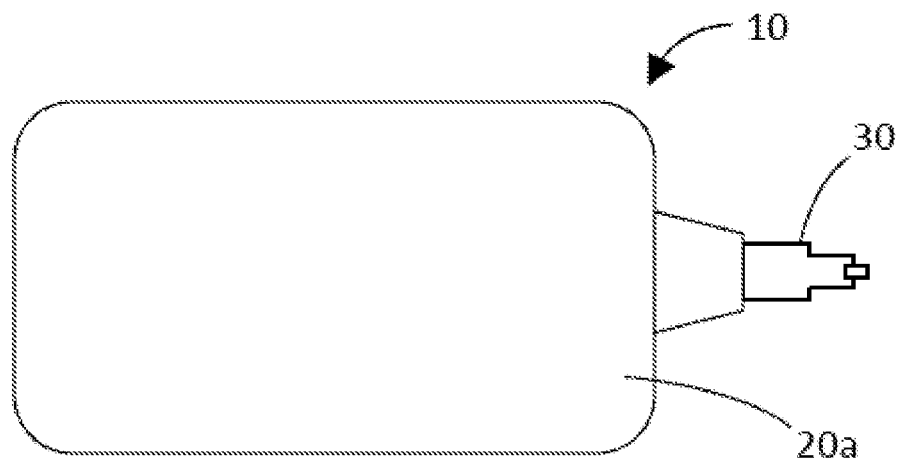
FIG. 1A is a functional block diagram of a hand-held resonance shift detector system according to one embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

In some embodiments, sensors for resonance shift detection of chemical and/or biological materials include two printed circuit boards ("PCB"), each with a single resonator die thereon, configured back-to-back such that the sensor has one sensing resonator and one reference resonator disposed on separate substrates. In the back-to-back PCB configuration, the backsides of two substantially identical configured PCBs are secured together such that the electrical contact section of each PCB is on one end of the sensor and each resonator on each PCB is on the other end of the sensor. The back-to-back PCB configuration provides a close proximity of the two resonators, which likely have closely matched resonant frequencies and phase responses. The close proximity ensures that the two resonators are subjected to substantially identical environmental conditions during a material sensing operation. The sensor effectively allows accurate phase shift or resonant frequency shift measurements and cancellation of environmental effects during material sensing operations. In some embodiments, the resonators on the PCB are off-center such that the back-to-back PCB configuration contains offset resonators with sufficient distance there between to reduce cross talk between the two resonators and not affect the flow of the sample liquid.

In some embodiments, the sensors for resonance shift detection include back-to-back PCB configurations utilizing two substantially different PCBs. In one aspect of the present invention, the resonator on one PCB is off-center while the resonator on the other PCB is centered. In this configuration, the reference and sensing resonators may still have sufficient distance there between to reduce cross talk between the two resonators. In another aspect of the present invention, the resonators on the two PCBs are such that the back-to-back PCB configuration results in the reference and sensing resonators being directly opposed. Cross talk between the resonators may be reduced or eliminated by the resonators being sufficiently separated or other means for cross talk elimination.

In some embodiments, the sensing resonator is coated with a different material than the reference resonator depending upon the material to be detected. By merely changing the coating on the resonators, the resonance shift detection system allows universal use for various diagnostic testing of chemical and/or biological materials without changing any of the other system structural components.

Sensors for resonance shift detection of chemical and/or biological materials effectively allow fast response times for the detection of the respective chemical and/or biological material, in the field detection capabilities, small sample sizes, minimally trained individuals, low direct and indirect costs, and electronically transmittable data.

In accordance with these and other aspects of the present invention, there is provided a sensor with a back-to-back paddle configuration, wherein each paddle includes a printed circuit board and at least one sensing resonator assembly and at least one reference resonator assembly, and at least a portion of the sensor within a sensor housing assembly, wherein the sensor housing assembly includes a sample channel for the introduction of the liquid sample to the at least one sensing resonator and at least one reference resonator.

In some embodiments, the resonance shift detection system includes a reusable handheld battery or solar-powered electronic instrument, and an easily mounted disposable sensor that may be contained within a sensor housing assembly. The sensor has a biological coating that specifically binds with the desired target molecule and provides the mechanism of detection and quantification. A specimen (whole blood, urine, saliva, or any other liquid) is drawn into the single-use sensor within the sensor housing assembly. Signals returned from the sensor (i.e. a change in phase or resonant frequency of the RF wave) indicate if the target is present, and if present, its concentration. For each analysis, a new sensor is attached to the instrument.

In some embodiments, the resonance shift detection system utilizes radio frequency resonators operating in shear wave mode. As these resonators operate they generate radio frequency waves that propagate into the liquid layer above the resonator. Changes in the viscosity of this liquid layer result in changes in the resonant characteristics of the resonator. The resonator surface is coated with a detection molecule such as a target specific antibody. As the sensor is exposed to a sample, binding of the target to the antibody causes a change in the resonance characteristics of the resonator. The rate of this change can then be used to give either a qualitative (yes/no) to identify presence, and a quantitative result (mg/dL) to determine concentration.

In some embodiments, each sensor has two resonators—a test (sensing) and a reference resonator. The reference resonator serves as an internal control and accounts for resonance changes resulting from non-specific binding, noise, or other changes in environmental conditions. The sensors are very small, thus enabling several resonators to be mounted on a single disposable sensor for testing several infectious agents or multiple pathogens at the same time on a single specimen such as multiple viral infections, several bio-warfare agents, several food or environmental contaminants, or the precise identification of an influenza virus' subtype.

In some embodiments, the rate of the resonance change varies with the concentration of the target. The rate of change of resonant frequency or phase angle for the most concentrated sample occurs faster than the lowest concentrated sample.

In some embodiments, the resonance shift detection system provides the user with a simple diagnostic testing platform that is inexpensive enough for worldwide deployment and provides several features and advantages over existing diagnostic testing systems, including, at least:

|  | Existing Systems | Present Invention |
| --- | --- | --- |
| Results | 10 to 30 minutes | 60 seconds or less |
| Instrument Cost | $2,000-$5,000 | $150-$250 |
| Size and portability | Large, not field portable | Size of cell phone, portable |
| Number of Steps | Multiple, many manual | One, automated |
| Sensitivity | Insensitive lateral flow | Highly sensitive sensor |
| Requires reagents/supplies | Yes | No |
| Complexity | Complex | Simple |
| Requires skilled operator | Yes | No |
| Environment | Lab/Institutional Setting | Any Environment |

The resonance shift detection system is ideal for detecting pathogens, proteins and bio-molecules in whole blood, urine, saliva, water, and other liquids and may be an effective tool for screening and diagnosing infections such as, for example, HIV, Smallpox, SARS, influenza (including swine flu or H1N1), and any other molecular biomarkers. The resonance shift detection system may make emerging proteomic diagnostics (measuring many biomarkers simultaneously to diagnose, monitor disease processes and therapy effectiveness over time) widely available and easy to use, providing an affordable means for measuring biomarkers for the early detection of various forms of cancer, heart disease or stroke, the discovery of metabolic diseases, the monitoring of tissue and organ health during recovery and rehabilitation, and for the examination of treatment effectiveness and compliance in chronic diseases, as well as a host of other applications.

Figure 1B:
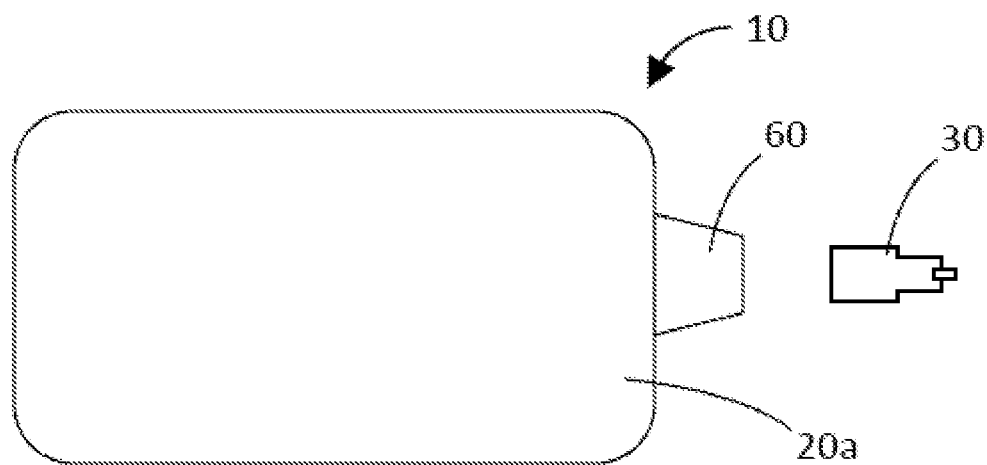
FIG. 1B is a functional block diagram of the hand-held resonance shift detector system of FIG. 1A with the sensor detached from the interconnector according to one embodiment.
Figure 1C:
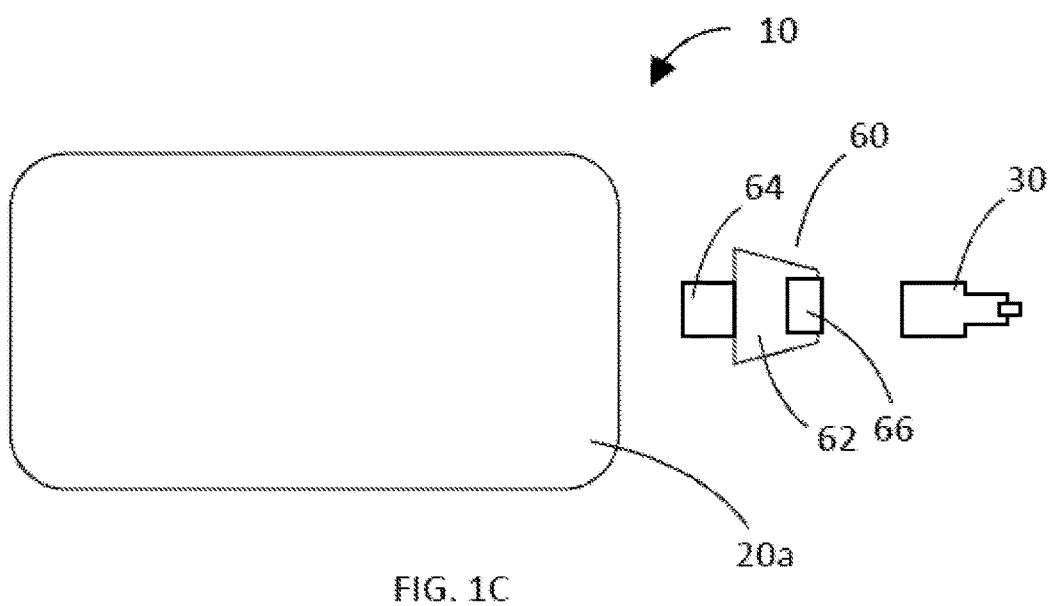
FIG. 1C is a functional block diagram of the hand-held resonance shift detector system of FIG. 1A with the sensor detached from the interconnector and the interconnector detached from the instrument.
Figure 1D:
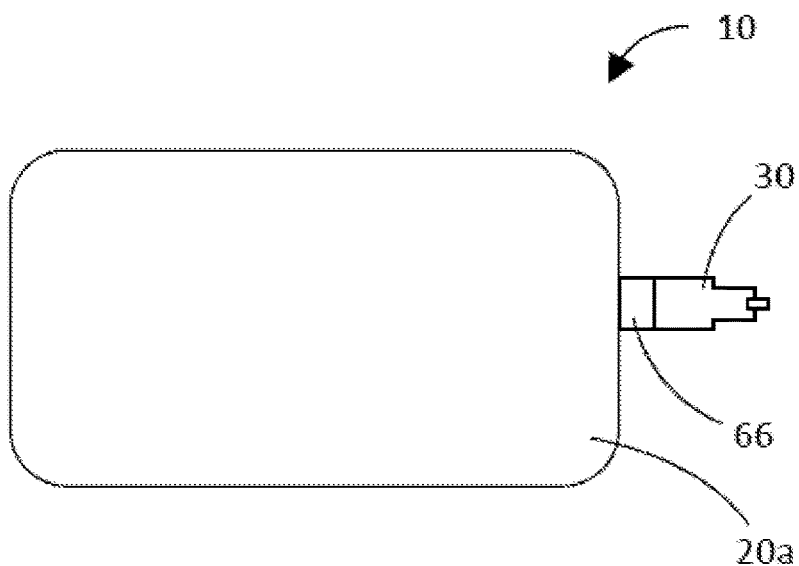
FIG. 1D is a functional block diagram of another hand-held resonance shift detector system of the present invention in which the resonance shift detector system and sensor are directly connected to each other with a connector mounted on the instrument board and without an interconnector according to one embodiment.

Referring now to the figures, the components of the resonance shift detector system of the present invention are illustrated. In some embodiments, the resonance shift detector system can be relatively small in size to be portable such that it can be utilized in the field for specific diagnostic testing applications. In some other embodiments, the resonance shift detector system can be configured for diagnostic testing in a laboratory setting. As shown in FIGS. 1A-1C, the resonance shift detector system 10 is illustrated in a hand-held or portable configuration that includes an instrument 20a capable of being interfaced with a sensor 30 by an interconnector 60, which can be used for point of need diagnostic testing in the field. As shown in FIG. 1D, the resonance shift detector system 10 is illustrated in a hand-held or portable configuration that includes an instrument 20a with a sensor connector 66 that is capable of directly electrically interfacing with sensor 30.

Figure 2:
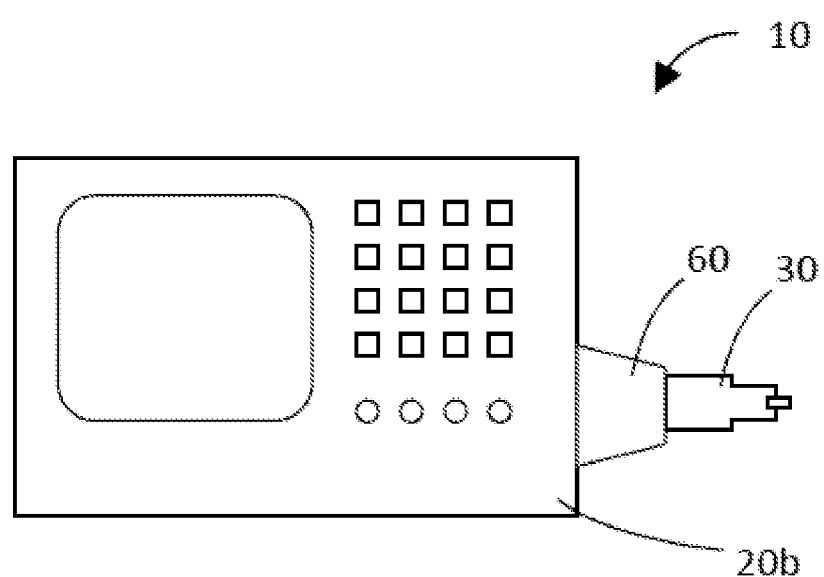
FIG. 2 is a diagram of a laboratory bench resonance shift detector system according to one embodiment of the present invention.

As shown in FIG. 2, the resonance shift detector system 10 is illustrated in a laboratory-bench or more permanent configuration that includes an instrument 20b, such as a Network Analyzer, capable of being interfaced with a sensor 30 by an interconnector 60. The sensor 30 mounted on an interconnector 60 and coupled to a laboratory-bench instrument 20b, such as a Network Analyzer, allows diagnostic testing in a laboratory setting, quality control testing of a batch of sensors during production, and/or the development of coatings on the sensor 30 for target material diagnostic testing.

The instrument 20, including, but not limited to hand-held instrument 20a and laboratory-bench instrument 20b, may have means for connection to the internet or otherwise transferring information, such as one or more USB ports, wireless connection, or the like.

Figure 3A:
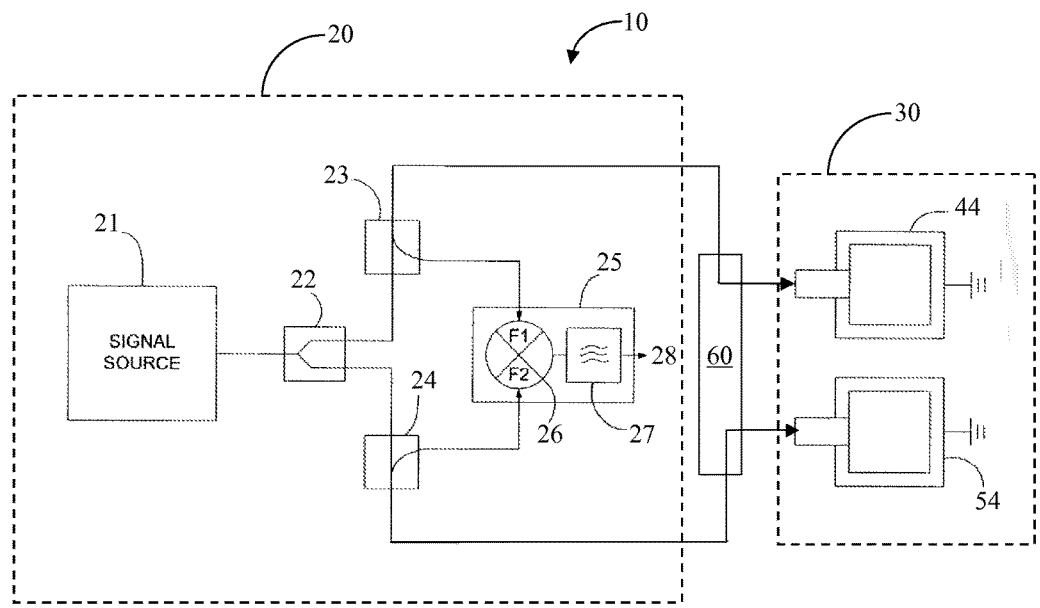
FIG. 3A is a schematic view of the resonance shift detector system according to one embodiment of the present invention with the interconnector located outside the instrument.
Figure 3B:
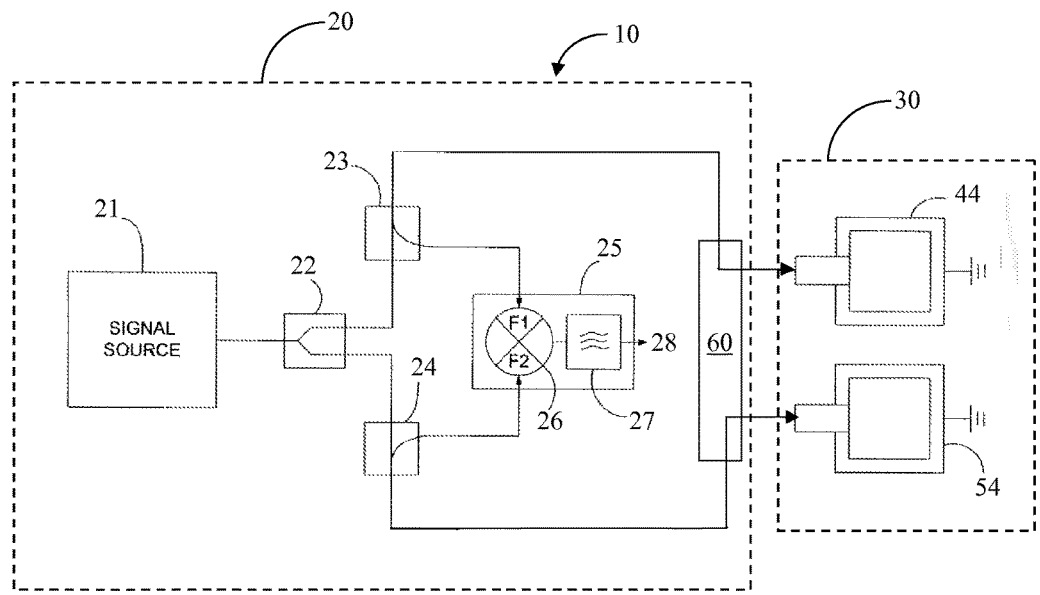
FIG. 3B is a schematic view diagram illustrating the resonance shift detector system of one embodiment with the interconnector located inside the instrument.

FIGS. 3A and 3B also show the instrument 20, whether a hand-held instrument 20a or a laboratory-bench instrument 20b, capable of being interfaced to the sensor 30 by the interconnector 60. The sensor 30 has a one-port sensing resonator 44 and a one-port reference resonator 54. A one-port resonator has an electrode that is used for both signal input and output. The other electrode of the one-port resonator is typically grounded. The hand-held instrument 20 generally includes a signal source 21 that provides an input signal of a frequency which is within the overlapping portion of the resonant bands of the resonators and in some aspects is set equal to the average of the resonance frequencies of the two resonators. The input electrical signal provided by the signal source 21 is split by a power divider 22 and the split signals are coupled through couplers 23, 24 to the respective sensing and reference resonators 44, 54. In this example embodiment, the phase angle of each resonator is the resonant characteristic that is being monitored. The output signals of the resonators are directed to the phase detector 25 by the respective couplers 23, 24 as sensor and reference signals. Both the input electrical signals and the output signals of the resonators pass through the interconnector 60 between the couplers 23, 24 and the respective sensing and reference resonators 44, 54. The phase detector 25 processes the sensor and references signals to produce an output signal indicative of a phase difference between the sensor and reference signals, which is caused mainly by the binding of the material being detected on the surface of the sensing resonator 44. In some embodiments, a separate signal source 21 can provide an input signal of a frequency for each of the respective resonators, which would eliminate the use of a power provider 22.

In one example embodiment, sensing and reference resonators 44, 54 are resonator assemblies that each include a piezoelectric crystal that is about 150-300 microns wide, and are formed on a silicon substrate, which is about 0.5×1 mm in size. The silicon substrate is mountable on a printed circuit board using solder bumps on a surface opposite the surface on which the sensing and reference resonators are formed (e.g., a "flip-chip" configuration).

The phase detector 25 in the illustrated embodiment includes a double-balanced mixer 26 (or a mathematic multiplier) which receives the sensor and reference signals. The output of the mixer 26 is passed through a low-pass filter 27 which eliminates a time dependent term and leaves only the DC term as the output 28 of the phase detector 25. As provided in more detail in U.S. Pat. No. 5,932,953, which is incorporated by reference herein, the resulting measured phase shift change can be used to derive the total amount of the material bound on the surface of the sensing resonator 44. In some embodiments, the signal source 21 generates an analog signal and the phase detector 25 generates either an analog or a digital output signal 28 after receiving the signal and reference signals and processing the information therefrom. In some embodiments, the signal from each respective resonator 44, 54 is directed to a separate respective phase detector 25, each respective phase detector 25 processing the respective sensor or reference signal to produce a phase signal indicative of a phase shift that are then compared to each other to determine the net difference in phase shift between the sensing and reference resonators, which is caused by the binding of the material being detected on the surface of the sensing resonator 44. Although this illustrative example describes a phase shift detection embodiment, it should be understood that other suitable arrangements may be implemented by persons skilled in the art that detect changes in another resonance characteristic, such as changes in resonant frequency, while implementing aspects of the invention described herein (which are generally applicable to resonance sensors of different types).

Figure 4A:
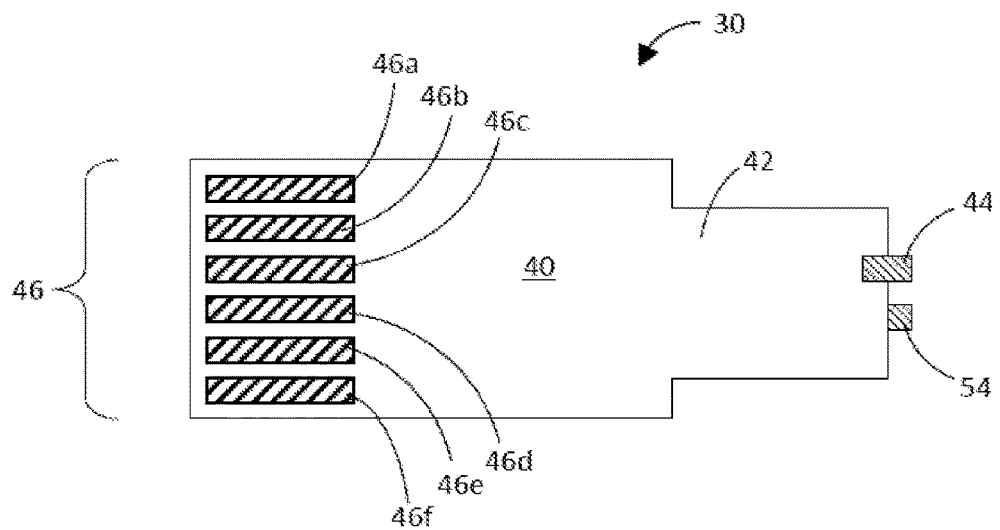
FIG. 4A is an illustration of a sensor having a back-to-back paddle configuration according to one embodiment.
Figure 4B:
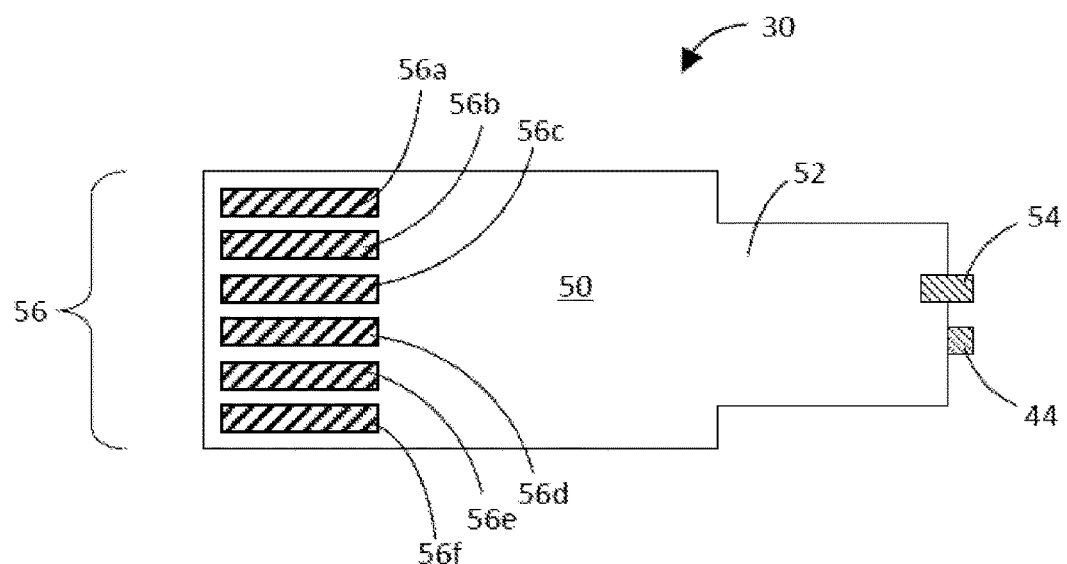
FIG. 4B is another illustration of the other side of the sensor of FIG. 4A.
Figure 5:
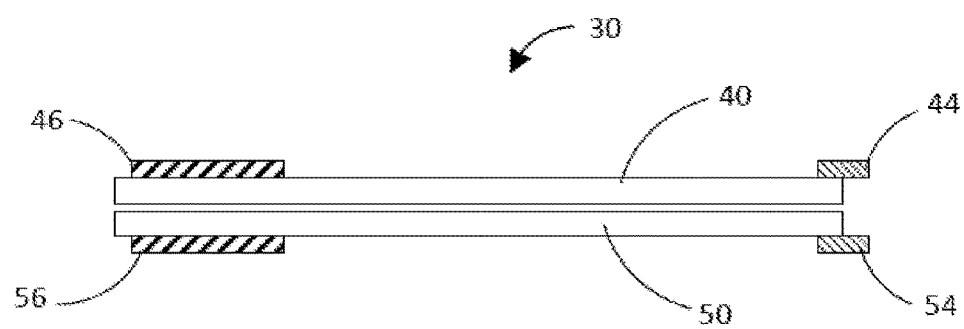
FIG. 5 is a side perspective view illustration of the sensor in FIGS. 4A-4B further illustrating the back-to-back paddle configuration embodiment.

In some embodiments, as shown in FIGS. 4A-4B and 5, sensor 30 comprises a first paddle 40 mounted in a back-to-back paddle configuration with a second paddle 50. The first paddle 40 and the second paddle 50 have essentially the same configuration such that the back-to-back paddle configuration results in a sensor 30 with a symmetrically opposed configuration. In some embodiments, each paddle comprises a substrate such as a printed circuit board with at least one resonator assembly mounted thereon. As illustrated in the figures, the first paddle 40 contains a first printed circuit board 42 with a sensing resonator assembly 44 mounted thereon on one end and a contact set 46 located on the opposite end. The second paddle 50 contains a second printed circuit board 52 with a reference resonator assembly 54 mounted thereon on one end and a contact set 56 located on the opposite end. Both the sensing resonator assembly 44 and the reference resonator assembly 54 may be cantilevered over the end of the respective printed circuit board 42, 52. In some aspects, the sensing resonator assembly 44 is coated with a test reagent that binds to or captures the specific material to be detected during the diagnostic testing. In some aspects, the reference resonator assembly 54 is coated with a reference reagent that does not bind with or otherwise capture the specific material to be detected during the diagnostic testing. The resonator assembly 44, 54 cantilevered over the end of the respective printed circuit board 42, 52 provides full access of the resonator 44*a*, 54*a* to facilitate reagent coating applications as well as exposure to the testing sample during diagnostic testing.

The sensor 30 may be of various shapes and sizes. In some embodiments, the sensor 30 with back-to-back paddles 40, 50 has the shape illustrated in FIGS. 4A-6C, which allows the resonator side of the sensor 30 to be inserted into a well of a standard 96 well plate. For instance, paddles 40, 50 can be approximately 2-3 cm along their longitudinal dimension, and 0.5-1.5 cm along their transverse dimension. In some embodiments, the two ends of the sensor 30 (contact set end and resonator end) are different widths such that there is a shoulder region that prohibits the sensor 30 from being inserted too far into a well of the standard 96 well plate. In some embodiments, the two ends of the sensor 30 are the same width, as illustrated for example in FIG. 11L.

In some aspects, as illustrated in FIGS. 4A-4B, the resonator assembly 44, 54 is attached to the printed circuit board 42, 52, respectively, in an off-center configuration. The off-center configuration allows an offset between the resonator assemblies 44 and 54 in the back-to-back paddle configuration, which may reduce cross talk during operation and not prevent the flow of the liquid sample during diagnostic testing. In some aspects, the resonator assemblies 44 and 54 are configured such that they are directly offset in the back-to-back paddle configuration, whether the resonator assemblies 44 and 54 are centered on the respective printed circuit board or otherwise off-set such that they at least partially overlap in the back-to-back paddle configuration.

While the foregoing description has identified the paddles 40, 50 of containing either one of a sensing resonator assembly or reference resonator assembly on a printed circuit board, the back-to-back paddle configuration allows the sensor 30 to contain one or more resonators on each of the respective printed circuit boards 42, 52. For instance, in one type of embodiment, paddle 40 contains two or more sensing resonators and paddle 50 contains two or more reference resonators. In other embodiments, paddles 40, 50 each contain at least one sensing resonator and at least one reference resonator. In related embodiments, paddles 40,50 may each contain various configurations of one or more resonators (sensing and/or reference), or paddle 40 or paddle 50 contains one resonator while the other contains more than one resonator. As indicated by the foregoing, various arrangements of sensing resonators and reference resonators on the respective printed circuit board 42, 52 to constitute the paddles 40, 50 is contemplated by the present invention.

In some embodiments, as shown in FIGS. 4A-4B, the contact sets 46, 56 contain six contacts 46*a*-46*f* and 56*a*-56*f*, respectively. Contacts 46*a* and 56*a* connect to the ground plane 47, 57, respectively, as shown in FIG. 6C. Contacts 46*b* and 56*b* are connected to the signal conductor 49, 59, respectively (shown in FIG. 6C) by a via 49' to the internal portion of the respective printed circuit board 42, 52 and are connected to the signal contacts 43*d*, 53*d* by a via 49". Contacts 46*c*, 46*d* and 56*c*, 56*d* connect to the ground plane 47, 57, respectively, as shown in FIG. 6C. Contact pairs 46*e* and 46*f* in FIG. 4A, or contact pairs 56*e* and 56*f* in FIG. 4B, are connected to each other.

In some embodiments with more than one resonator on the respective paddle 40, 50, one of ordinary skill in the art will appreciate the number of contacts on in contact sets 46, 56 will depend upon the number of resonators and that each resonator will be connected to a signal contact in the respective contact set 46, 56. In such embodiments, there may be one or more ground contacts connected to the ground plane 47, 57 and a signal contact connected to the respective resonator. In some embodiments, the contact configuration of ground, signal, ground provides an advantage of reducing signal loss, although only one ground per one signal provides electrical continuity.

Figure 6A:
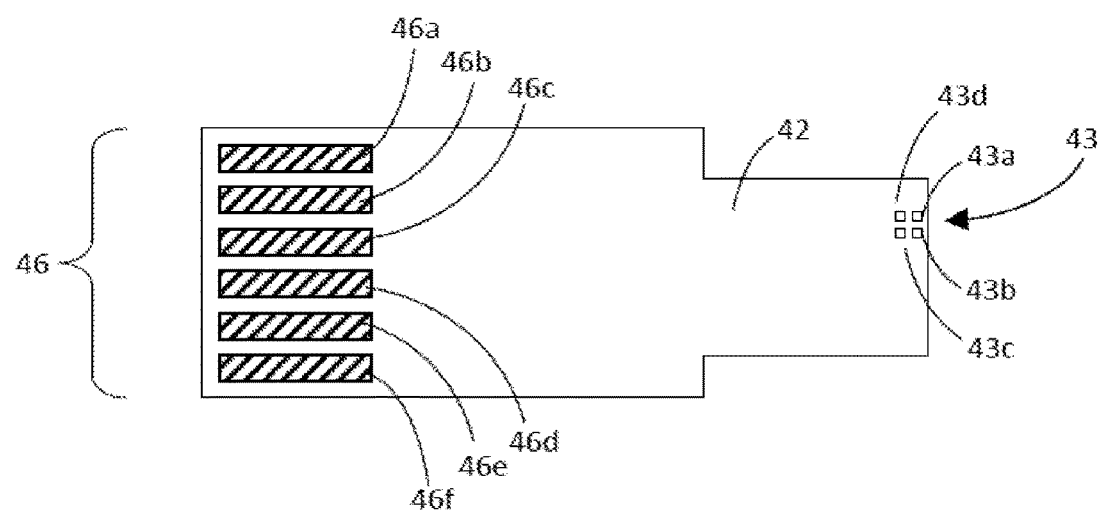
FIG. 6A is a schematic top view of the front side of a printed circuit board from which the back-to-back paddle configuration embodiment is constructed according to one embodiment.
Figure 6B:
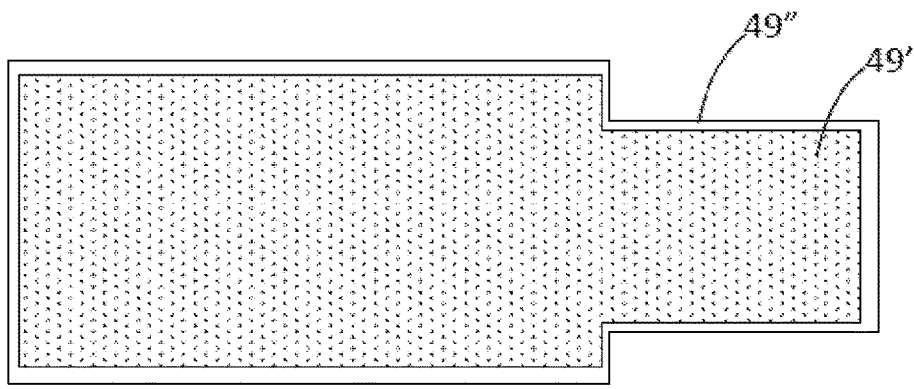
FIG. 6B is a schematic top view of the back side of the printed circuit board in FIG. 6A.
Figure 6C:
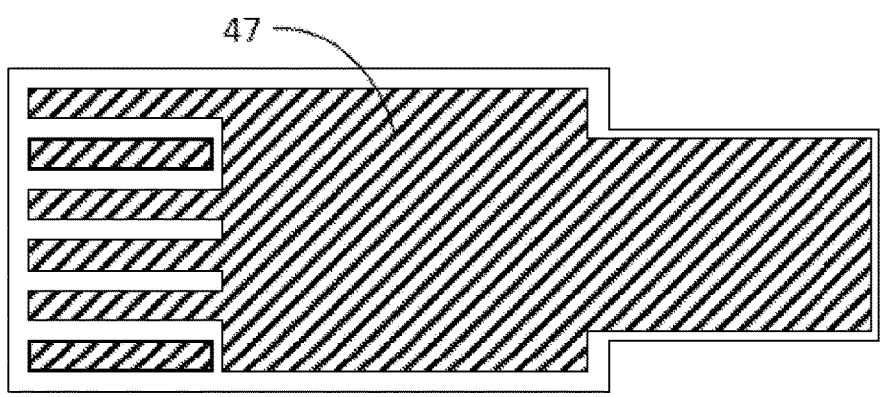
FIG. 6C is a schematic view of the various layers of the printed circuit board in FIGS. 6A-6B.
Figure 6C:
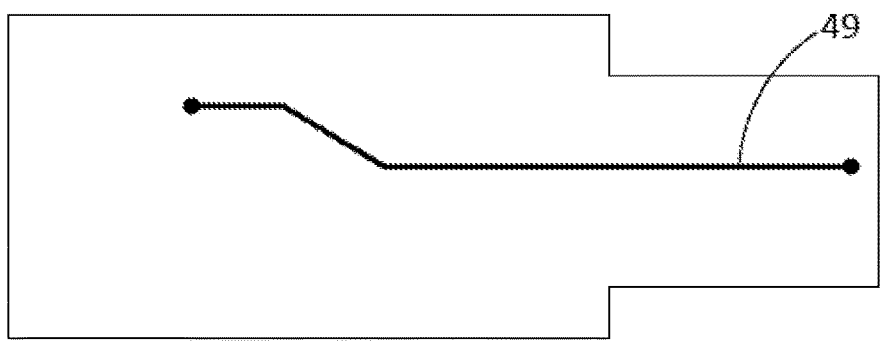

FIGS. 6A-6C further illustrate a printed circuit board 42, 52 and the layers thereof, of the sensor 30. Since the sensor 30 in some embodiments is comprised of the back-to-back paddle configuration of paddles 40 and 50 that have essentially the same configuration, the following description with respect to printed circuit board 42 of paddle 40 shall be understood to equally apply to the printed circuit board 52 of paddle 50. In some embodiments, both the sensing resonator assembly 44 and the reference resonator assembly 54 attach to the respective printed circuit board 42, 52 by a set of reflow solder bonds. As shown in FIG. 6A, the printed circuit board 42 contains a set of solder pads 43, with solder pads 43a-43c being connected to the ground plane 47 and solder pad 44d being signal connected to signal contact 46b by signal conductor 49. Now referring to FIG. 6C, the first panel illustrates the vias 49', 49" that connect the signal contacts 46b, 43d, respectively, to the signal conductor 49 in the internal portion of the printed circuit board 42. The second panel illustrates the top conductor layer with ground plane 47. The third panel illustrates the mid-conductor layer with signal conductor 49 surrounded by a ground conductor. The fourth panel illustrates the bottom conductor layer with a ground plane. The fifth panel illustrates the ground stitching to connect all of the ground planes in the second, third and fourth panels together. The sixth panel illustrates the top solder mask with a devoid space for the contact set. The seventh panel illustrates the bottom solder mask, and the eighth panel illustrates the routing pattern to give the printed circuit board 42 its shape. As illustrated by the three conductor layers, the signal conductor 49 is a strip line sandwiched on all sides by ground conductor, which essentially is the equivalent of a coaxial conductor. In some embodiments, this conductor layer configuration creates a 50 ohm impedance matched structure.

Figure 7A:
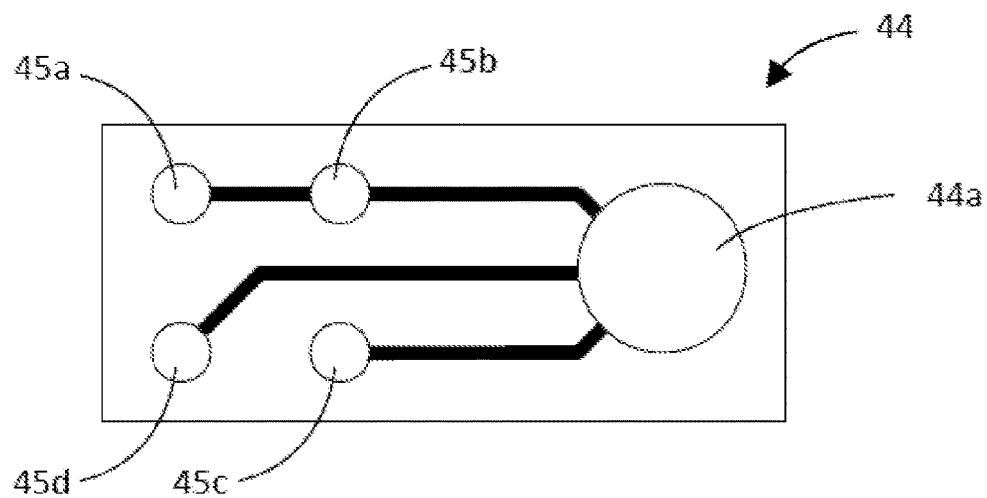
FIG. 7A is a schematic top view of a resonator assembly according to one embodiment of the present invention.
Figure 7B:
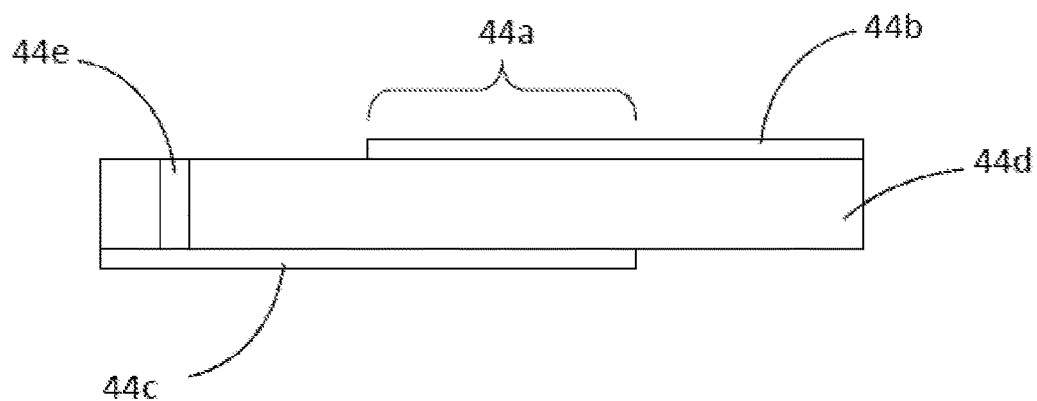
FIG. 7B is a schematic of a cross sectional view of the resonator assembly of FIG. 7A.

The solder pads 43, 53 on the respective printed circuit board 42, 52 are attached to a resonator assembly, whether a sensing resonator assembly or a reference resonator assembly. Referring now to FIG. 7A, the top surfaces of a resonator assembly is illustrated, which is equally applicable to both sensing resonator assemblies and reference resonator assemblies. For ease of reference, the following description refers to the sensing resonator assembly 44, although the description is equally applicable to the reference resonator assembly 54. As illustrated in FIG. 7A, the top surface of the sensing resonator assembly 44 contains a set of solder bumps 45. Solder bumps 45a-45c are connected to ground within the resonator assembly 44. Solder bump 45d is connected to the resonator 44a by way of a via 44e through the piezoelectric layer 44d and a resonator conductor 44c between, which is further illustrated by the cross sectional view in FIG. 7B. When the resonator assembly 44 is attached to the printed circuit board 42 to form paddle 40, solder pad 43a and solder bump 45a are connected, solder pad 43b and solder bump 45b are connected, solder pad 43c and solder bump 45c are connected, and solder pad 43d and solder bump 45d are connected. The resonator assembly 44 is also cantilevered over the edge of the printed circuit board 42 to allow the resonator 44a to be exposed to the surrounding environment during the testing process. In some embodiments, the solder pads 45 may be on a different side of the resonator assembly 44 than the resonator 44a, such that the resonator assembly 44 does not have a cantilevered configuration.

In building impedance matched resonators, the relative surface area of the resonator 44a is directly related to the frequency at which the resonator resonates, with higher frequency resonators having a smaller surface area and lower frequency resonators having a larger surface area. Accordingly, it is contemplated that resonators with various resonant frequencies may be used depending upon the desired resonant frequency and any regulatory restrictions on the frequencies available to be used. The thickness of the piezoelectric layer also affects frequency with a thinner piezoelectric resonating at a higher frequency than a thicker layer. In various embodiments, resonance frequencies range from 500 MHz to 2.5 GHz or higher. For example, in certain embodiments operation at resonant frequencies up to 5 GHz, or 10 GHz, is contemplated.

Since the back-to-back paddle configuration allows the sensing resonator 44 and the reference resonator 54 to be located in a close proximity with each other, the two resonators are subjected to substantially identical environmental conditions during a material sensing operation, which allows for accurate resonance shift measurements and effective cancellation of the environmental effects. Environmental effects that may be cancelled may be a result of viscosity, pH, temperature, particulates, and any other environment conditions within the sample that will affect the sensing resonator 42 during diagnostic testing.

In some embodiments, the sensor 30 contains a sensor housing assembly 32 as illustrated in FIGS. 8A-10B. The sensor housing assembly 32 may include a body portion 33 that substantially contains at least a portion of the back-to-back paddles 40, 50 and a cover portion 34 that operably engages with the body portion 33. In some embodiments, the body portion 33 and the cover portion 34 are relatively the same size such that the back-to-back paddles 40, 50 are about equally contained within each portion 33, 34. In some embodiments, the contact sets 46, 56 are exposed and not surrounded by the sensor housing assembly 32, as illustrated in FIGS. 8A-8D and 10A-10B. In some other embodiments, as illustrated in FIGS. 9A-9B, the sensor housing assembly 32 extends over at least a portion of the contact sets 46, 56 while still allowing connection thereto.

In some aspects, the cover portion 34 is bonded to the body portion 33, such as by ultrasonic welding. The sensor housing assembly 32 may also contain a sample channel 35 that provides the ability for the sample aliquot to be brought into direct contact with the sensing and reference resonator assemblies 44, 54 of the sensor 30. In some embodiments, the sample aliquot is introduced to the sensing and reference resonator assemblies 44, 54 by capillary action. In some embodiments, the volume of the sample aliquot introduced within the sensor housing assembly 32 is between about 15 microliters to about 50 microliters. In some aspects, the sample volume within the sensor housing assembly 32 will be known and have a relatively reproducible volume between diagnostic tests such that quantitative assessment of the targeted material being sensed may be ascertained. As illustrated in FIGS. 9A-10B, the sensor housing assembly 32 may also contain a venting mechanism to effectuate the introduction of the sample aliquot to the sensing and reference resonator assemblies 44, 54.

Figure 8A:
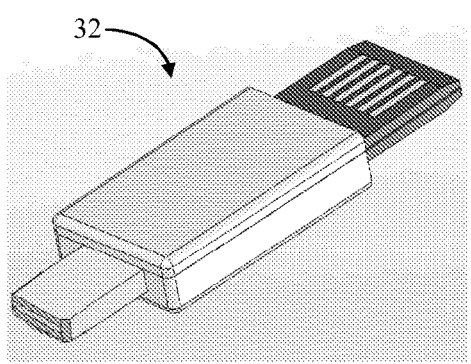
FIG. 8A is a perspective schematic of a sensor assembly within a sensor housing assembly according to one embodiment of the present invention.
Figure 8B:
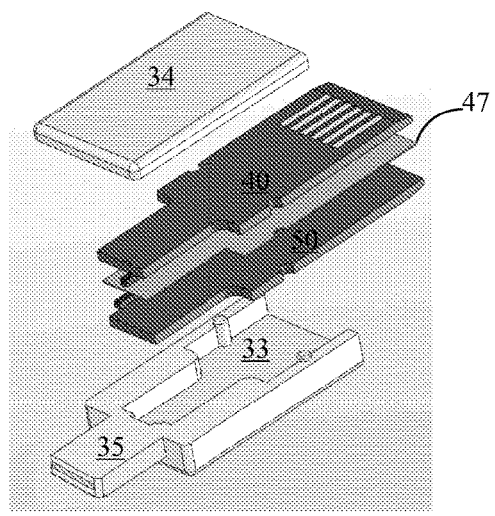
FIG. 8B is an exploded perspective schematic of the sensor assembly within the sensor housing assembly of FIG. 8A.
Figure 8C:
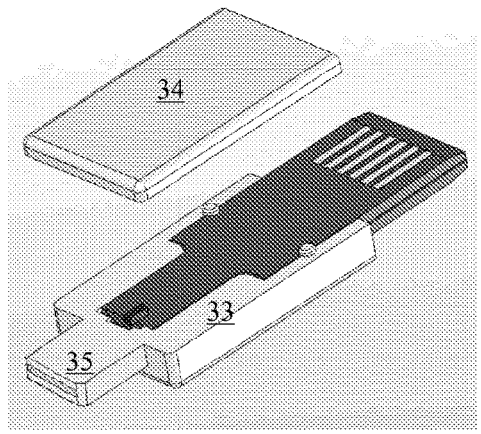
FIG. 8C is a perspective schematic of the sensor assembly within the sensor housing assembly of FIG. 8A with a top portion of the sensor housing assembly removed.
Figure 8D:
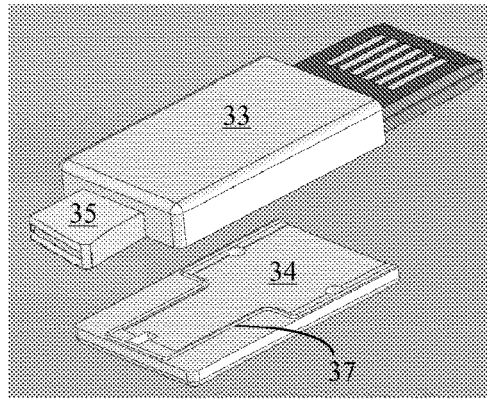
FIG. 8D is another perspective schematic of the sensor assembly within the sensor housing assembly of FIG. 8A with the top portion of the sensor housing assembly removed.

In some embodiments, as illustrated in FIG. 8B, paddles 40, 50 are mounted together in the back-to-back configuration with a bonding agent 47, such as a tape, adhesive, glue, or the like. In one aspect, the bonding agent 47 also provides a liquid barrier that prevents the liquid sample from penetrating between the paddles 40, 50 and migrating towards the contact sets of the sensor 30. The body portion 33 and/or the cover portion 34 may also contain energetic director means for creating a gasket seal when ultrasonically welded that also prevents the migration of the sample aliquot on the top or side surfaces of the paddles 40, 50. For example, as illustrated in FIG. 8D, the cover portion 34 contains energy directors 37 with corresponding energy directors on the body portion (not shown) for ultrasonic welding the body portion 33 and cover portion 34. In some embodiments, the sensor 30 and sensor housing assembly 32 will be used for a single diagnostic test and are disposable. In some aspects, the back-to-back paddle configuration allows the sensor 30 to be small in size with a width being about three-tenths of an inch or smaller and the length being about one inch or smaller.

Now referring back to FIGS. 1A-1C and 2, the interconnector 60 is capable of simultaneously interfacing with the instrument 20 and the sensor 30 to enable the electrical coupling of the instrument 20 and the sensor 30. As illustrated best in FIG. 1C, the interconnector 60 includes a printed circuit board 62 on which is mounted an instrument connector 64 and a sensor connector 66. The instrument connector 64 electrically interfaces to the instrument 20 and the sensor connector 66 electrically interfaces to the sensor 30. In some embodiments, the interconnector 60 is located outside the housing of the instrument 20, as illustrated in FIG. 3A. In some embodiments, the interconnector 60 is located inside the housing of the instrument 20, as illustrated in FIG. 3B. The instrument connector 64 and sensor connector 66 may consist of any of the connectors known to one of ordinary skill in the art, including printed circuit board edge connectors or SubMiniature version A ("SMA") connectors, as shown in FIGS. 1A-1C and 2. In some embodiments, both the instrument connector 64 and the sensor connector 66 are printed circuit board edge connectors that electrically interface with printed circuit board edge connectors on the instrument and sensor, respectively. As discussed above, the sensor 30 may contain sets of contacts 46, 56. The sensor connector 66 may also contains the same number of contacts on the top receiving portion and on the bottom receiving portion to operably receive the same number of contacts on the sensor 30. The top and bottom receiving portion of the sensor connector 66 may also have the same type of ground and signal configuration as the corresponding contacts on sensor 30.

The instrument connector 64 and the sensor connector 66 allow the interconnector 60 to be removed from the resonance shift detector system 10 in order to be replaced without affecting the integrity of the instrument 20 and/or the sensor 30. Since the sensor 30 is removable from the interconnector, and in some embodiments intended for a single use and therefore disposable, the interconnector 60 may need to be replaced as a result of normal use. The repeated insertion of a sensor 30 into the interconnector 60 may result in the sensor connector 66 wearing out under normal use conditions. Other instances may arise resulting in the advantage of a modular configuration of the resonance shift detector system 10, including other issues arising with respect only to the interconnector 60, the interconnector 60 containing software applications that need to be updated, and the like.

In some embodiments, the interconnector 60 contains a read-only memory on the printed circuit board 62. The read-only memory may serve to setup the instrument for specific market applications by including software or identification information that allows the instrument 20 to understand the particular use of the resonance shift detector system 10 as it relates to the sensor 30. For instance, the read-only memory may contain information or explicit instructions for the interpretive logic of the instrument that relates to the output signal of the sensor 30, which may serve to limit the resonance shift detector system 10 to specific applications, such as limited only to use in veterinary applications, as an example. Besides being limited to specific market applications, the information on the read-only memory may also serve to limit the resonance shift detector system 10 to specific sub-market applications or range of sub-market applications. For instance, within the medical market, certain individuals may not be licensed or qualified to conduct a wide range of diagnostic testing; but instead, be limited to certain diagnostic testing. As a result, the market segment identification information may limit the use of the resonance shift detector system 10 to only those proper diagnostic testing applications.

In some embodiments, the interconnector 60 includes an industry standard means for capturing patient identification information, such as a bar code or RFID reader. In clinical and hospital settings, the RFID reader may be used for patient identification, identifying the clinic or hospital, healthcare person, and the like.

In some embodiments, besides the sensing resonator 44 and reference resonator 54, paddle 40 and paddle 50 may also differ from each other in the contact sets 46, 56 to provide an "on-off" switch mechanism when the sensor 30 is inserted into interconnector 60. For the "on-off" switch mechanism, contact pairs 46e and 46f on paddle 40 are connected to each other, but paddle 50 does not contain the symmetrically mirror-image opposed contact pairs 56e and 56f. Instead, paddle 50 would contain contacts 56a-56d in the same relative position as shown in FIG. 4B with contacts 56e and 56f being absent. When the sensor 30 with this contact set configuration is inserted into the interconnector 60, each of contacts 46a-46d engages a respective contact on the sensor connector 66 and contact pairs 46e and 46f engages two respective contacts on the sensor connector 66. On the opposite side of the sensor 30, each of the contacts 56a-56d also engages a respective contact on the sensor connector 66. The contact pairs 46e and 46f engaging two respective contacts on the sensor connector 66 while the opposing contacts in the sensor connector 66 are not engaged acts as an "on-off" switch for the instrument 20. The instrument 20 will turn on when the sensor 30 is inserted into the sensor connector 66, and the instrument 20 may be turned off when the sensor 30 is removed from the sensor connector 66. While the sensor 30 may contain more contacts on one side than the other, the resonance shift detector system 10 may be configured such that there is no side specific insertion of the sensor 30 into the sensor connector 66. Instead, the "on-off" switch mechanism will work no matter how the contact set side of the sensor 30 is inserted into the sensor connector 66. This eliminates the need for the user of the resonance shift detector system 10 to know the proper insertion of the sensor 30 into the interconnector 60 other than the end of the sensor 30 with the contact sets 46, 56 being inserted into the sensor connector 66. In some embodiments, the sensor connector 66 and sensor 30 are configured to have a lock-and-key type configuration, such that the user is only able to insert the sensor 30 into sensor connector 66 in the correct configuration.

The foregoing contact set configuration can also provide a sensor side identification feature, such that the instrument 20 is able to identify the side of the sensor 30 containing the sensing resonator 44 and the side containing the reference resonator 54. In some embodiments, the sensor side is determined by the relationship of the contact sets 46, 56 with the contacts on the sensor connector 66 much the same as the "on-off" switch mechanism. The side of the sensor 30 with the six contacts will engage the respective six contacts on that specific side of the sensor connector 66 receiving the sensor 30 indicating the sensing resonator 44 is located on that side of the sensor 30 and/or the side of the sensor 30 with only four contacts will only engage four respective contacts on that specific side of the sensor connector 66 receiving the sensor 30 indicating the reference resonator 54 is located on that side of the sensor 30.

While both the "on-off" switch mechanism and sensor side identifier feature have been described with respect to the paddle 40 containing both a sensing resonator 44 and the six contacts 46a-46f, the sensor 30 may alternatively be configured such that paddle 50 containing the reference resonator 54 contains six contacts 56a-56f to provide the "on-off" switch mechanism and/or sensor identifier feature. Similarly, the contact sets may be configured to provide the "on-off" switch mechanism and/or sensor identifier feature without necessarily containing six contacts on one of the paddles 40, 50. Instead, it is contemplated that the sensor 30 may contain more or less than six contacts without departing from the scope and spirit of the present invention.

Figure 11A:
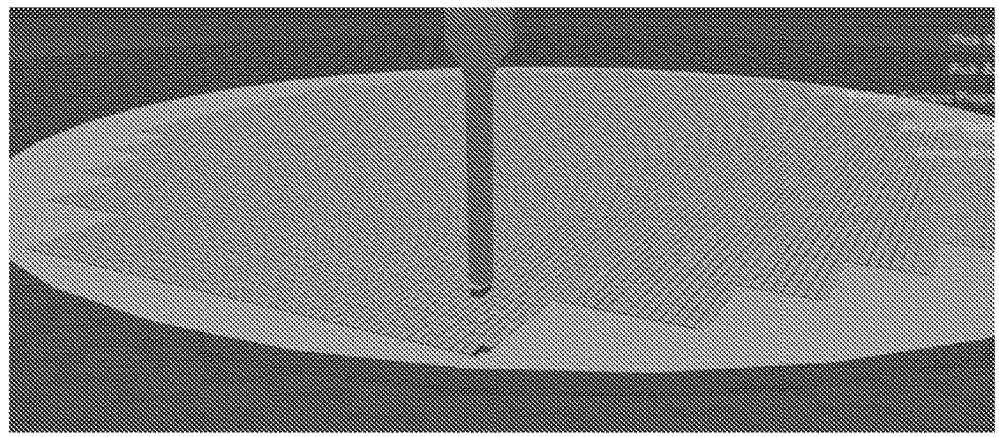
FIGS. 11A-11M illustrate a process for the manufacture of the sensor according to one embodiment of the present invention.
Figure 11B:
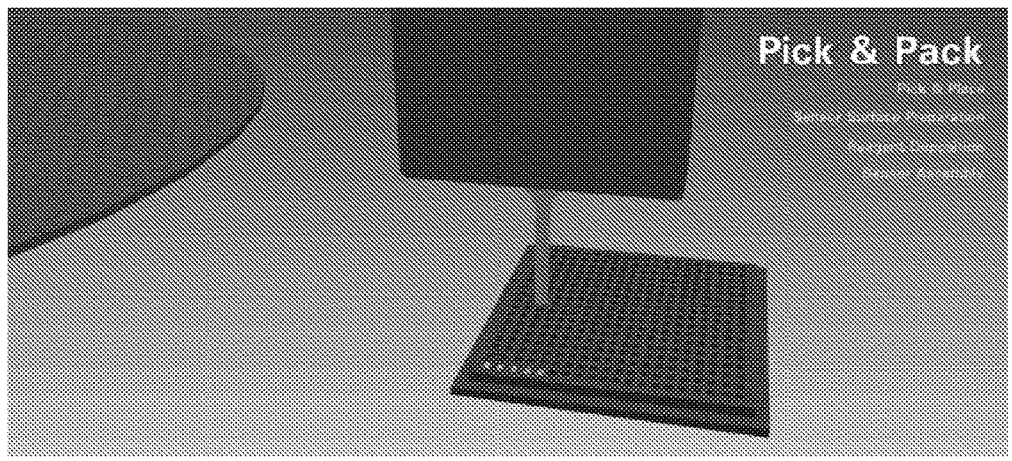
Figure 11C:
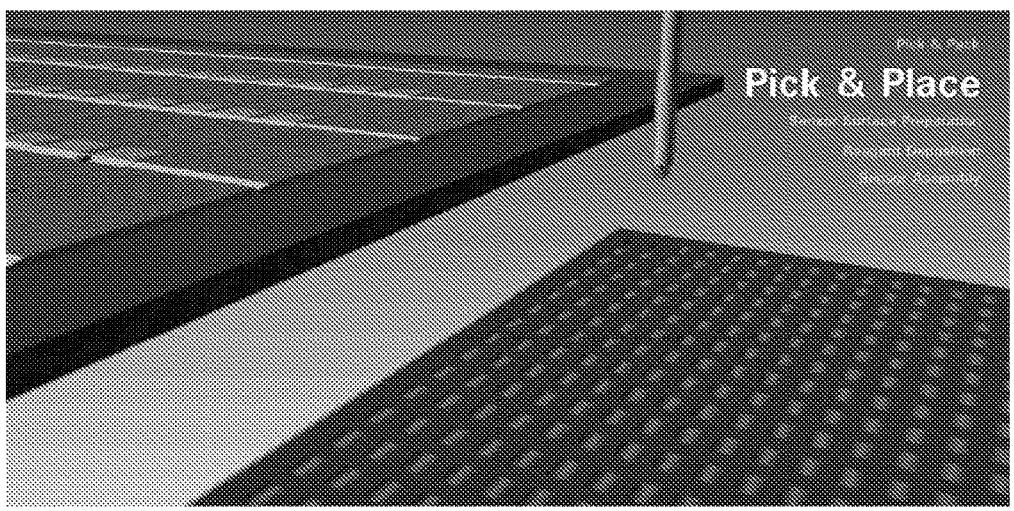
Figure 11D:
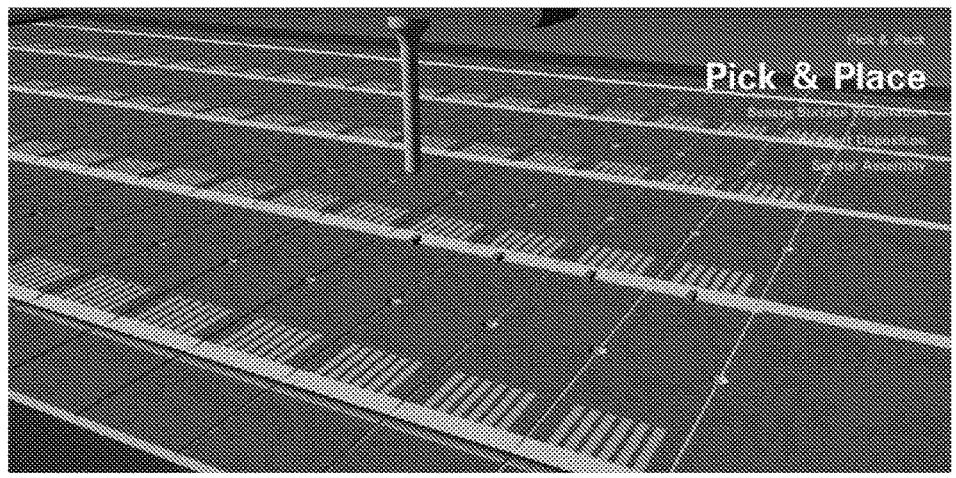

One process for the manufacture of the sensor 30 is illustrated in FIGS. 11A-11M. In FIG. 11A, individual resonator assemblies may be picked off of a wafer and placed into a waffle pack as illustrated in FIG. 11B. In some aspects, the wafer is pre-tested such the functional and non-functional resonator assemblies are known, and the non-functional resonator assemblies may be discarded. After the resonator assemblies are packed into the waffle pack, they are then picked, as shown in FIG. 11C, and placed onto the respective printed circuit board, as shown in FIG. 11D, at a position where solder flux is spotted onto the printed circuit board, which serves to adhere the resonator assembly to the printed circuit board until the melting and reflow of the solder is conducted within a heated oven. In another protocol, the individual resonator assemblies are picked off of the pre-tested wafer and packed into a tape-and-reel configuration having a linear strip. This process provides an alternative to the step of picking each resonator out of the waffle pack to be placed onto a printed circuit board.

Figure 11E:
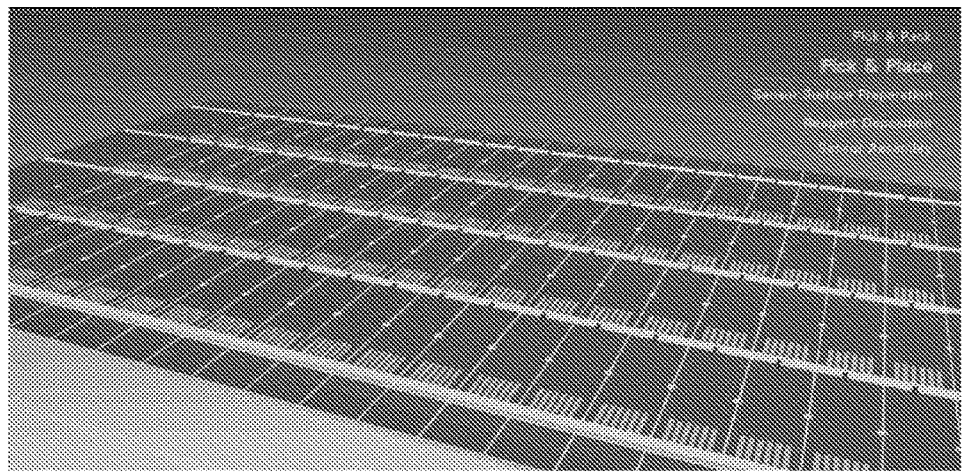

FIG. 11E illustrates that the paddles may be manufactured from a panel of printed circuit boards with the resonator assemblies adhered thereto. In another protocol, instead of a panel of printed circuit boards, the paddles are manufactured from a continuous tape configuration that would allow numerous side-by-side paddle configurations. This continuous tape configuration combined with the tape-and-reel configuration allows for efficient manufacture of numerous paddles.

Figure 11F:
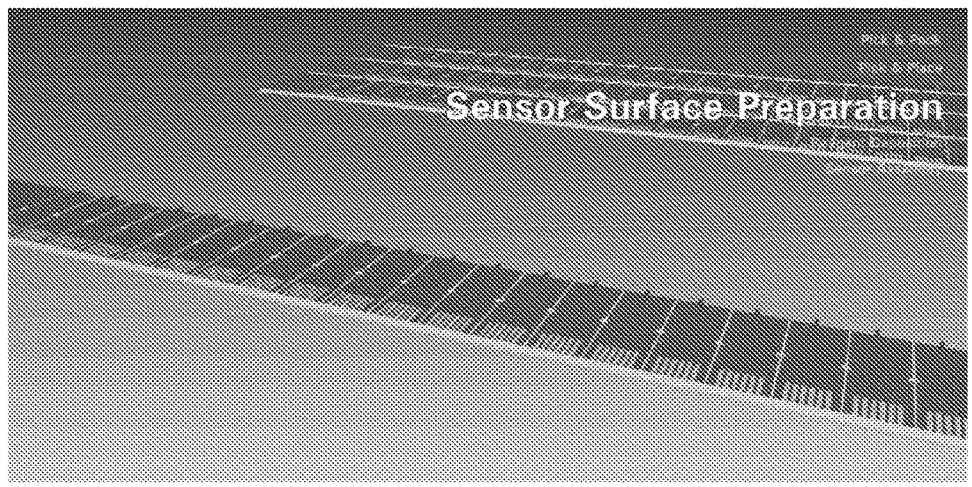
Figure 11G:
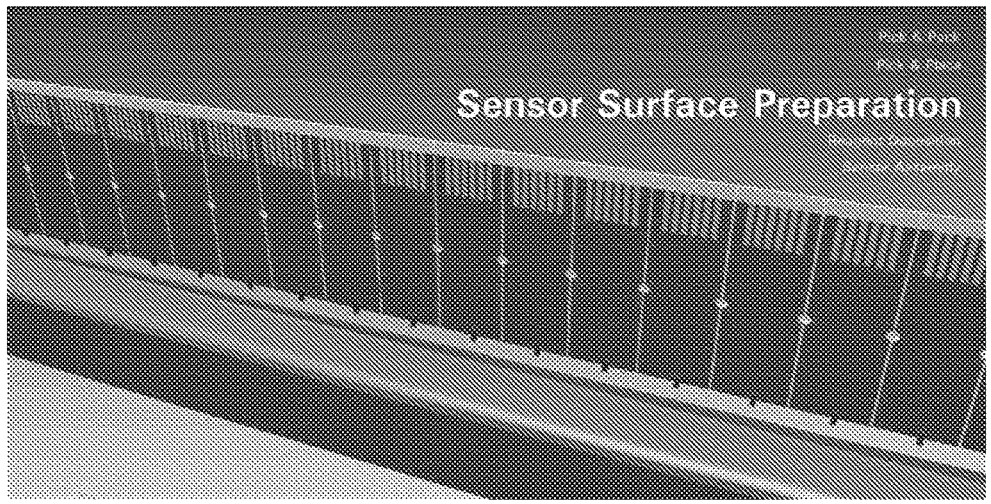
Figure 11H:
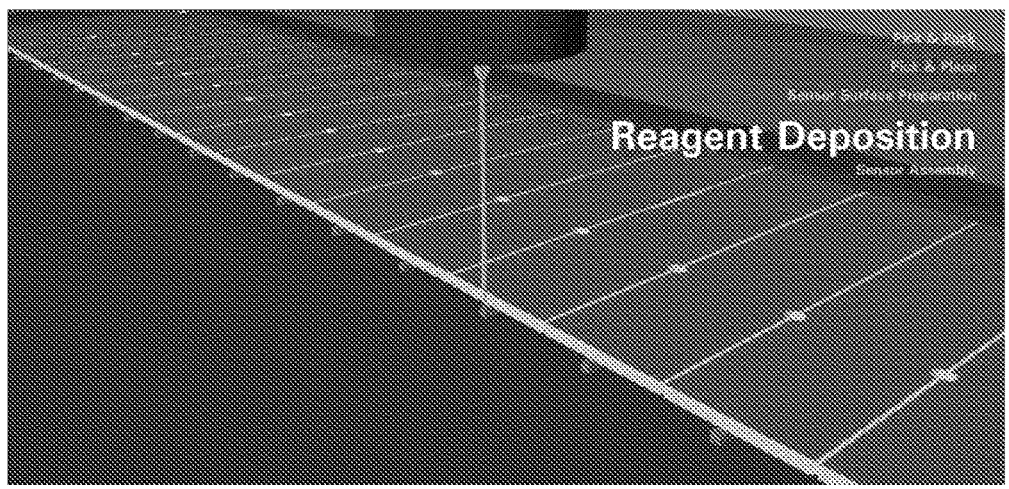
Figure 11I:
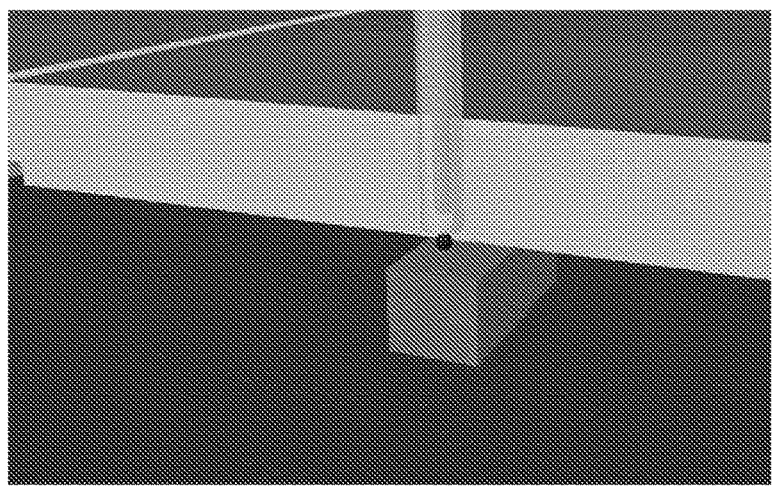
Figure 11J:
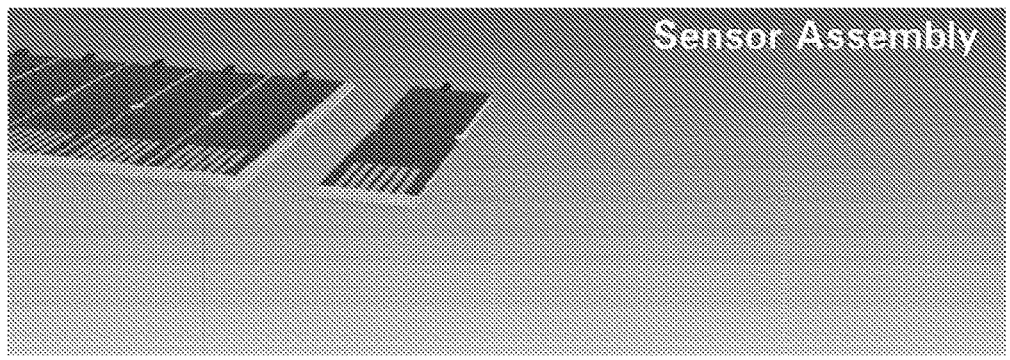

After a panel of paddles is created, a strip or row of paddles is removed from the panel with all of the resonator assemblies aligned on a single edge, as illustrated in FIG. 11F. The edge of the strip or row of paddles containing the resonator assemblies may then be immersed into a narrow trough, set of test tubes, or other container configuration containing one or more desired reagents for preparing the resonator assembly surface, as illustrated in FIG. 11G. The resonator assemblies cantilevered over the edge of the printed circuit board facilitates this step. In one aspect, the preparing reagent may be a self-assembling monolayer that provides a reactive group on the surface of the resonator assembly to which a wide range of desired materials may be adhered. In some aspects, the desired materials may be proteins, DNA, aptamers, lipopolysacharides, biologically active molecules, or other capture ligands, depending upon the material to be detected. While the individual materials or ligands assembled on the surface of the resonator assembly may be on the nano-level scale, the diagnostic testing operates on an aggregate scale on the micro-level by virtue of a micron-sized resonator as the base substrate for the adhered materials. As illustrated in FIGS. 11H-11I, the desired material may be placed onto the reactive surface of the resonator assembly and bonded with the reactive monolayer to create the desired coating on the respective sensing or reference resonator. Any excessive amounts of the desired material not bound to the reactive monolayer may be washed away. After the resonator assemblies are coated with the desired material, the individual paddles are separated from the strip or row of paddles, as shown in FIG. 11J.

Figure 11K:
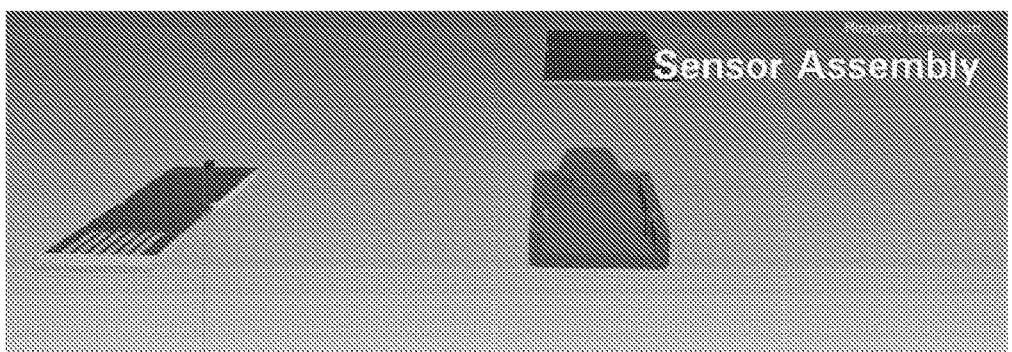
Figure 11L:
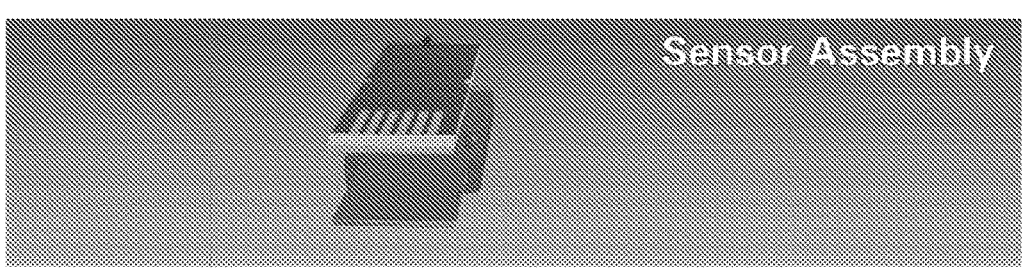
Figure 11M:
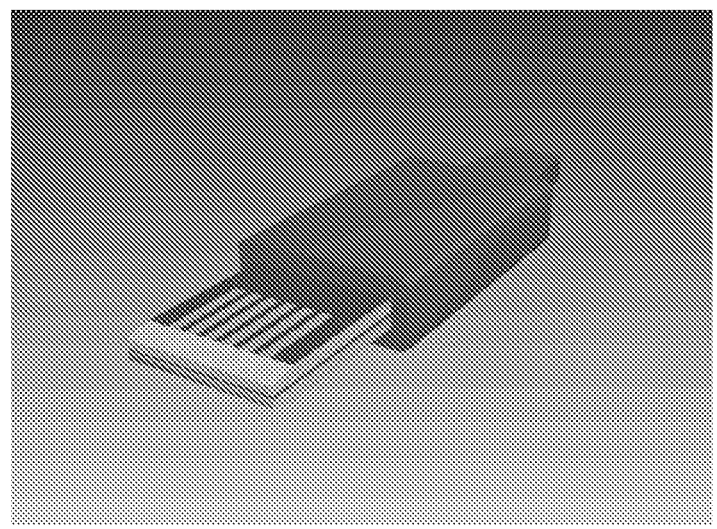

Once the individual paddles are created, a desired sensing paddle 40 and a desired reference paddle 50 is provided and then placed into a sensor housing assembly 32 in a back-to-back paddle configuration as illustrated in FIGS. 11k-11L with an intermediate bonding agent as discussed above. The resultant sensor 30 within a sensor housing assembly 32 is illustrated in FIG. 11M.

As illustrated in the foregoing disclosure, the back-to-back paddle configuration provides a platform to provide numerous different types of diagnostic testing depending upon the sensing paddle and reference paddle. Since there may be numerous sensing paddles and reference paddles with different coatings on the resonator assemblies, a sensor may be provided for a specific diagnostic test merely by providing the appropriate sensing paddle and reference paddle from inventory. In some aspects, the reference paddle may be matched with numerous different types of sensing paddles depending upon the diagnostic test to be performed by the resultant sensor. Accordingly, the back-to-back paddle configuration provides a universal diagnostic testing platform.

Figure 12A:
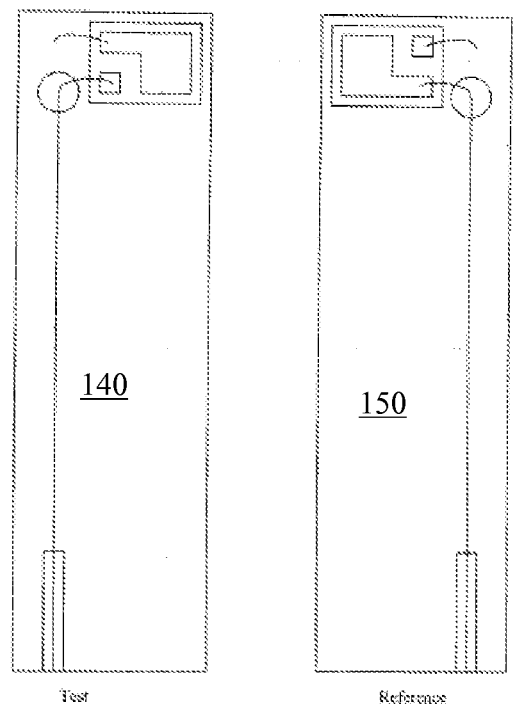
FIG. 12A is a schematic of another embodiment of a sensor configuration of the present invention.
Figure 12B:
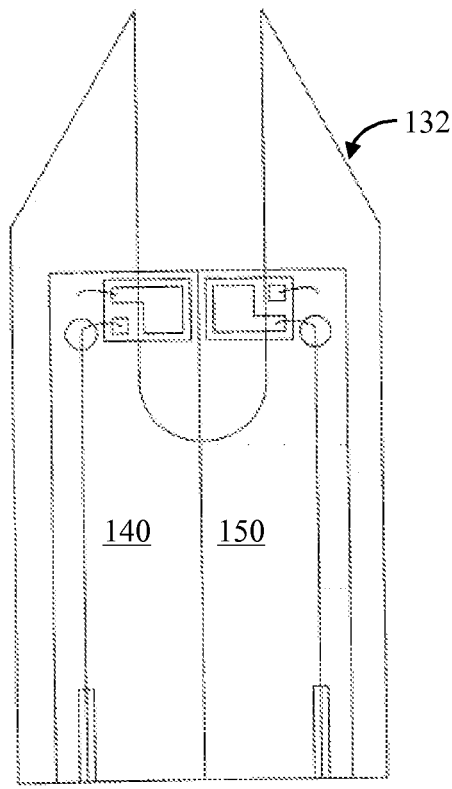
FIG. 12B is a schematic of the sensor configuration of FIG. 12A within a sensor housing assembly of the present invention.

Referring now to FIGS. 12A-12B, in some embodiments, the sensor 30 configuration may be an adjacent or side-by-side paddle configuration with a first paddle 140 mounted adjacent to a second paddle 150. While FIGS. 12A-12B illustrate mirror imaged paddles, the first paddle 140 and second paddle 150 may have the same relative configuration. In some embodiments, the sensor 30 may contain a sensor housing assembly 132 as illustrated in FIG. 12B. In some embodiments, the sensor 30 may comprise two or more back-to-back paddle configurations in a side-by-side configuration.

While the foregoing disclosure has referred to the sensor having at least one sensing resonator and at least one reference resonator disposed on a printed circuit board substrate, other substrates are contemplated by various embodiments of the present invention, including, for example multichip modules, the silicon wafer of the resonator assembly, or the like. The respective substrate would connect the respective resonator to the instrument through an impedance match conductor.

During the use of the resonance shift detector system 10, including the portable field-detection embodiments, the insertion of the sensor 30 into the sensor connector 66 may turn on the instrument 20 and the interface screen on the instrument 20 will indicate to the user that the resonance shift detector system 10 is ready to obtain a sample.

During the sampling process, the sensor 30 may be introduced into a liquid or gaseous sample, or the sample aliquot may be introduced to the sensing and reference resonators 44, 54 by way of a sensor housing assembly. The liquid sample for the diagnostic test may include blood, urine, serum, saliva, water, or any other liquid sample that may be of interest. As soon as the sample contacts the sensing and reference resonators 44, 54, there is a change in signal from the resonators 44, 54. The instrument 20 is waiting to receive the change in signal, and once the change in signal is detected, the instrument 20 begins the interpretative sequence of collecting data. The instrument 20 continues to collect data until either (i) the instrument 20 times out because the signal has not changed, or (ii) depending upon the speed with which the signal changes, the instrument 20 will stop collecting data once enough data is received to give an interpretation of the diagnostic test. An interpretation of the diagnostic test may include an indication that the target material has been bound or captured onto the sensing resonator and a quantification of the target material.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

Any incorporation by reference of documents above is limited such that no subject matter is incorporated that is contrary to the explicit disclosure herein. Any incorporation by reference of documents above is further limited such that no claims that are included in the documents are incorporated by reference into the claims of the present application. The claims of any of the documents are, however, incorporated as part of the disclosure herein, unless specifically excluded. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A sensor for a biosensor instrument, the sensor comprising:
    a sensing resonator assembly and at least one sensing electrical contact in electrical communication with the sensing resonator assembly; and
    a reference resonator assembly and at least one reference electrical contact in electrical communication with the reference resonator assembly;
    wherein the sensing resonator assembly is mechanically arranged relative to the reference resonator assembly such that the sensing and reference resonator assemblies are on a proximal end of the sensor;
    wherein the at least one sensing contact is mechanically arranged relative to the at least one reference resonator contact such that the at least one sensing contact and the at least one reference contact are on a distal end of the sensor;
    wherein the sensing resonator assembly comprises at least one sensing resonator coated with a testing material that operably interacts with a target material, and wherein the sensing resonator is constructed such that it has a resonant frequency in the range of about 0.5 GHz to about 10 GHz; and
    a printed circuit board assembly defining a first surface and a second surface facing opposite the first surface, wherein the sensing resonator assembly is disposed on the first surface of the printed circuit board assembly and the reference resonator assembly is disposed on the second surface of the printed circuit board assembly.

2. The sensor of claim 1, wherein the reference resonator assembly comprises at least one reference resonator that does not operably interact with the target material.

3. The sensor of claim 1, wherein the reference resonator assembly comprises a resonator coated with a reference material.

4. The sensor of claim 1, wherein the proximal end of the sensor is sized to be inserted into a well of a standard 96 well plate.

5. The sensor of claim 1, wherein the sensing and reference resonator assemblies are positioned in a back-to-back configuration.

6. The sensor of claim 1, wherein the sensing and reference resonator assemblies are positioned in a side-by-side configuration.

7. A sensor for a biosensor instrument, the sensor comprising:
    a sensing resonator;
    a reference resonator; and
    a printed circuit board assembly defining a first surface and a second surface facing opposite the first surface, wherein the sensing resonator is disposed on the first surface of the printed circuit board assembly and the reference resonator is disposed on the second surface of the printed circuit board assembly;
    wherein the sensing resonator is mechanically arranged relative to the reference resonator such that the sensing and reference resonator assemblies are on an end of the sensor;
    wherein the sensing resonator is coated with a testing material that operably interacts with a target material, and wherein the sensing resonator is constructed such that it has a resonant frequency in the range of about 0.5 GHz to about 10 GHz.

* * * * *